US012685826B2

(12) United States Patent
Baillargeon et al.

(10) Patent No.: US 12,685,826 B2
(45) Date of Patent: *Jul. 21, 2026

(54) SHEATHS FOR NEEDLE DELIVERY

(71) Applicant: GYRUS ACMI, INC., Westborough, MA (US)

(72) Inventors: Jean-Martin Baillargeon, Seattle, WA (US); Christopher Ralph, Woodinville, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 957 days.

This patent is subject to a terminal disclaimer.

(21) Appl. No.: 17/812,881

(22) Filed: Jul. 15, 2022

(65) Prior Publication Data

US 2022/0347394 A1 Nov. 3, 2022

Related U.S. Application Data

(63) Continuation of application No. 16/070,567, filed as application No. PCT/US2016/063516 on Nov. 23, 2016, now Pat. No. 11,395,885.

(Continued)

(51) Int. Cl.
*A61M 5/32* (2006.01)
*A61B 1/267* (2006.01)
(Continued)

(52) U.S. Cl.
CPC ......... *A61M 5/3202* (2013.01); *A61B 1/2676* (2013.01); *A61B 8/12* (2013.01);
(Continued)

(58) Field of Classification Search
None
See application file for complete search history.

(56) References Cited

U.S. PATENT DOCUMENTS 5,336,178 A 8/1994 Kaplan et al.
5,785,689 A 7/1998 De Toledo et al.
(Continued)

FOREIGN PATENT DOCUMENTS

CN 108348279 8/2022
WO WO-2014125707 A1 8/2014

OTHER PUBLICATIONS

"German Application Serial No. 112016005402.5, Office Action mailed Jan. 31, 2024", with English Translation, 20 pgs.
(Continued)

*Primary Examiner* — Matthew Kremer
(74) *Attorney, Agent, or Firm* — Schwegman Lundberg & Woessner, P.A.

(57) ABSTRACT

A needle apparatus having a sheath with a protective hypo-tube insert and a method of making the needle sheath. An example needle apparatus includes a handle, a needle having a proximal end connected to the handle and a sheath. The sheath is configured to receive of the needle. The sheath includes a proximal end connected to the handle, a distal end, a lumen and the protective insert. The lumen passes from the proximal end to the distal end of the sheath. The protective insert is received within the lumen at the distal end of the sheath when force and/or heat are applied.

17 Claims, 3 Drawing Sheets

Related U.S. Application Data

(60) Provisional application No. 62/259,732, filed on Nov. 25, 2015.

(51) Int. Cl.

| | |
|---|---|
| *A61B 8/12* | (2006.01) |
| *A61B 10/02* | (2006.01) |
| *A61B 10/04* | (2006.01) |
| *A61B 17/34* | (2006.01) |
| *A61B 90/00* | (2016.01) |

(52) U.S. Cl.
CPC .......... *A61B 10/0283* (2013.01); *A61B 10/04* (2013.01); *A61B 17/3478* (2013.01); *A61B 2010/045* (2013.01); *A61B 2090/0801* (2016.02); *A61B 2090/3925* (2016.02); *A61M 2205/0266* (2013.01); *A61M 2207/00* (2013.01)

(56) References Cited

U.S. PATENT DOCUMENTS

| | | | | |
|---|---|---|---|---|
| 5,899,850 | A * | 5/1999 | Ouchi | .................... A61B 10/04 |
| | | | | 600/104 |
| 6,264,676 | B1 * | 7/2001 | Gellman | ............... H04L 12/413 |
| | | | | 606/232 |
| 6,785,689 | B1 | 8/2004 | Daniel et al. | |
| 10,064,606 | B1 | 9/2018 | Williams et al. | |
| 11,395,885 | B2 * | 7/2022 | Baillargeon | ........... A61B 10/04 |
| 2002/0183720 | A1 | 12/2002 | Hill et al. | |
| 2003/0093104 | A1 * | 5/2003 | Bonner | .............. A61B 17/3478 |
| | | | | 606/185 |
| 2003/0225312 | A1 * | 12/2003 | Suzuki | ............. A61B 17/00234 |
| | | | | 600/114 |
| 2004/0193140 | A1 | 9/2004 | Griffin et al. | |
| 2005/0215942 | A1 | 9/2005 | Abrahamson et al. | |
| 2005/0267490 | A1 | 12/2005 | Secrest et al. | |
| 2008/0183184 | A1 | 7/2008 | Kaye et al. | |
| 2009/0204005 | A1 | 8/2009 | Keast et al. | |
| 2010/0081965 | A1 | 4/2010 | Mugan et al. | |
| 2012/0061392 | A1 | 3/2012 | Beach et al. | |
| 2012/0289772 | A1 | 11/2012 | O'connell et al. | |
| 2015/0087994 | A1 | 3/2015 | Matsuno et al. | |
| 2016/0038348 | A1 | 2/2016 | Booth et al. | |
| 2016/0310669 | A1 * | 10/2016 | Harms | ............. A61M 5/31583 |
| 2016/0331222 | A1 | 11/2016 | Aoki et al. | |
| 2019/0022333 | A1 | 1/2019 | Baillargeon et al. | |

OTHER PUBLICATIONS

"German Application Serial No. 112016005402.5, Response filed May 31, 2024 to Office Action mailed Jan. 31, 2024", w english claims, 12 pgs.

"merriam-webster.com", collocate, [Online] Retrieved from the internet: <www.merriam-webster.com/dictionary/collocate>, (2021), 3 pgs.

* cited by examiner

SHEATHS FOR NEEDLE DELIVERY

CROSS-REFERENCE TO RELATED APPLICATIONS

This application is a Continuation of U.S. patent application Ser. No. 16/070,567, filed Jul. 17, 2018 and now issued as U.S. Pat. No. 11,395,885, which is a National Stage Application of PCT Application Serial No. PCT/US2016/063516, filed Nov. 23, 2016, which claims the benefit of priority to U.S. Provisional Patent Application No. 62/259,732, filed Nov. 25, 2015; the contents of which are incorporated herein by reference in their entireties.

BACKGROUND

Typically, needles are transported within an endobronchial ultrasound (EBUS) working channel using a sheath. Example sheaths are formed of polytetrafluoroethylene (PTFE). To protect the EBUS working channel, the interior of the sheath includes a coil at the distal end of the sheath. However, this configuration can result in the needle tip snagging or perforating the sheath the coil and in increased resistance in activating (advancing distally/moving forward) the needle. Also, manufacturing assembly of the coil to the PTFE sheath can be complicated by the coil's inherently low column strength, possibly necessitating the creation of a "pocket" where the coil is to be inserted. This process is a time-consuming and costly process.

SUMMARY

The present invention provides a needle sheath with a protective hypotube and a method of making the needle sheath. An example needle apparatus includes a handle, a needle having a proximal end connected to the handle and a sheath. The sheath receives the needle. The sheath includes a proximal end connected to the handle, a distal end, a lumen and a metal tube. The lumen passes from the proximal end to the distal end of the sheath. The metal tube is received within the lumen at the distal end of the sheath.

In one aspect of the invention, an outside diameter of the metal tube is greater than a diameter of the lumen of the sheath and/or an inside diameter of the metal tube is greater than or equal to a diameter of the lumen of the sheath.

In another aspect of the invention, the metal tube is stainless steel. The metal tube includes a plurality of cuts. The plurality of cuts are radial cuts, spiral cuts or a combination of both. The plurality of cuts may be overlapping cuts.

In still another aspect of the invention, the sheath is formed of a polymer, such as polytetrafluoroethylene.

In yet another aspect of the invention, an example method includes first applying heat to a polymer sheath for a needle. The sheath includes a lumen extending from a proximal end to a distal end, wherein the proximal end of the sheath is configured to be attached to a handle. Second, a force is applied to at least one of the sheath or a metal tube until the metal tube is fully received with in the sheath, wherein the sheath expands radially at a region occupied by the metal tube.

In still yet another aspect of the invention, an outside diameter of the metal tube is greater than a diameter of the lumen of the sheath before metal tube insertion and/or an inside diameter of the metal tube is greater than or equal to a diameter of the lumen of the sheath before metal tube insertion.

In a further aspect of the invention, the metal tube is stainless steel having a plurality of interrupted cuts made into the metal tube before combining with the sheath. The plurality of interrupted cuts are radial cuts, spiral cuts or a combination of both. The plurality of cuts may be overlapping cuts.

In still a further aspect of the invention, a thermal forming process is performed on the sheath distal from a distal end of the metal tube.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1-1 illustrates an side view of an aspiration device in a deactivated state in accordance with principles of the present invention;

FIG. 1-2 illustrates a side view of the aspiration device of FIG. 1-1 in an activated state;

FIG. 2 illustrates a close-up view of the distal end of a sheath used in the device shown in FIGS. 1-1 and 1-2;

DETAILED DESCRIPTION

Figures 1, 2:
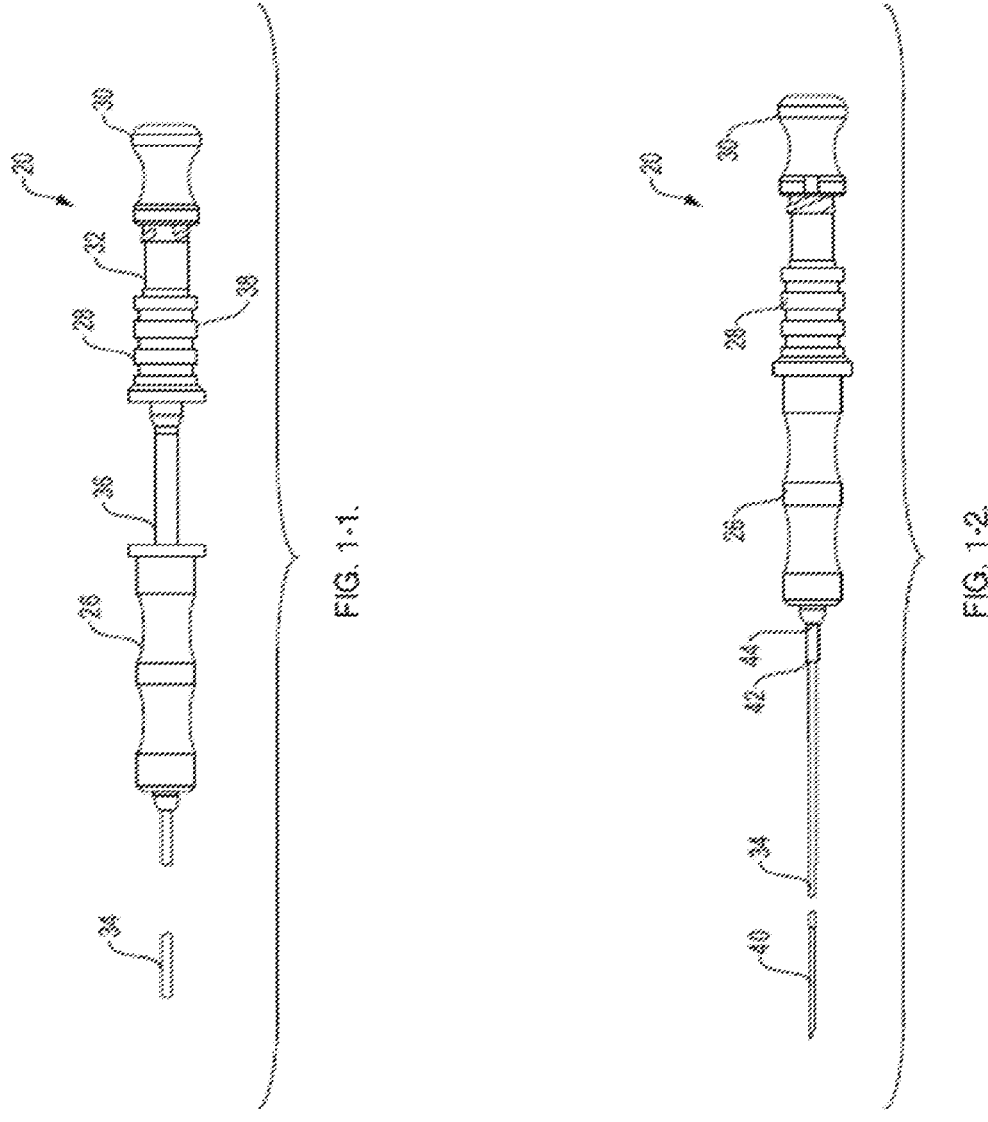
Figure 2:
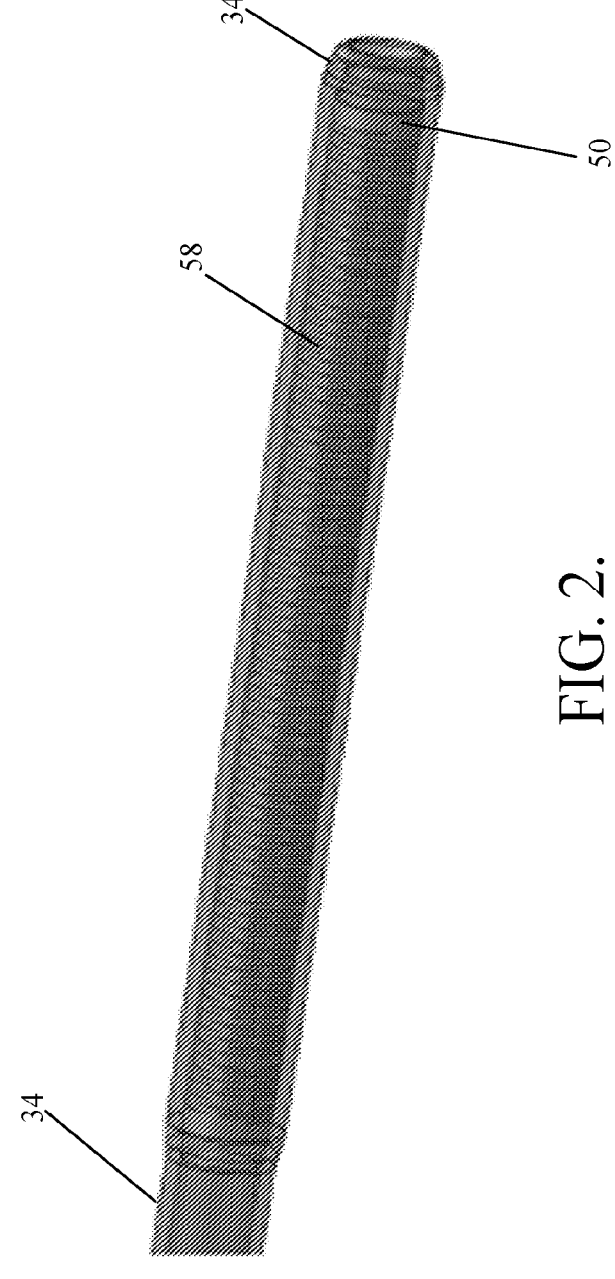

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description. The teachings herein may be used without limitation. In other words, the teachings herein may be used in any medical procedure. The teachings herein may be used for accessing any part of any anatomy. For example, one or more, or various vessels, passages, lumens, body cavities, tissue, organs, the like, or a combination thereof in humans and animals can be accessed using the teachings herein.

The teachings include a needle device for use in an endobronchial ultrasound (EBUS) system or in other delivery systems.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein.

While the teachings herein refer to and reference terms like "bronchoscope", "lymph node", "nodule", "device", "needle", and the like, it is understood that these terms are broad, and the teachings herein can be used without limitation. In other words, the teachings herein may be suitable for illuminating other vessels, passages, lumens, body cavities, anatomy, tissue, organs, the like, or a combination thereof in humans and animals. One or more devices may function to control motion of a needle, needle sheath and/or catheter, thus improving navigation. The one or more devices may include one or more bronchoscopes.

The one or more bronchoscopes may be or may provide a device for attaching to a steerable catheter that can allow a user to sample tissue within or around human lumen. The one or more bronchoscopes may provide for insertion, manipulation, and operation of various surgical instruments in the anatomy of a patient. The one or more bronchoscopes may provide for delivery of the catheter into the anatomy. The one or more bronchoscopes may be used to visually inspect a site of interest, like the airways and lungs of a patient. The one or more bronchoscopes may be used to examine, treat, and/or diagnose lung growth, lung problems, lung cancer, lymph node(s), atelectasis, suspected interstitial lung disease, a lung rejection after a lung transplant, and/or to remove fluid or mucus plugs from the airways of a patient. The one or more bronchoscopes may be at least partially flexible, at least partially rigid, or both. The one or more bronchoscopes may include one or more ultrasound probes.

One or more catheters may function to provide a channel, a lumen, an opening, and/or a passageway for one or more devices to be advanced and/or introduced into the anatomy. The one or more catheters may function to introduce into the anatomy one or more medical devices, needles, transbronchial needle aspiration devices, cytology brushes, biopsy forceps, guiding devices, ultrasonic probes, illumination devices, therapies (i.e., chemotherapy, proteinomics, microspheres, etc.), fiducials, the like, or a combination thereof. The one or more catheters may be used to remove or expel from the anatomy one or more devices, fluids, tissue samples, abnormalities, foreign matter, or a combination thereof. The one or more catheters may each contain one or more lumen. The one or more catheters may include one or more sections that are generally rigid, one or more sections that are generally flexible, or a combination of both. The one or more catheters may include one or more sections that are generally rigid, generally flexible, or a combination of both. The one or more catheters may be at least partially flexible, bendable, articulable, or a combination thereof so that access to regions of interest can be easily obtained. The one or more catheters may bend or articulate 15 degrees or more, 45 degrees or more, 60 degrees or more, 90 degrees or more, 110 degrees or more, or even 130 degrees or more. The one or more catheters may be fabricated from a metal alloy, such as stainless steel or Nitinol (nickel and titanium at various percentages), a polymer, nylon, silicon, or any other suitable material. An outer surface of the one or more catheters may include a lubricant to facilitate insertion into, and removal from, the anatomy, the bronchoscope, a working channel of the bronchoscope, or a combination thereof. The one or more catheters may be elongated tubular members. The one or more catheters may extend along a longitudinal axis, a catheter axis, or both. The one or more catheters may include a uniform cross section, or the cross section may vary, taper, widen, narrow, or a combination thereof. The cross section of the one or more catheters may be circular, oval, irregular, and/or any other suitable shape or configuration. The cross section of the one or more catheters may be expandable, collapsible, formable, deformable, or a combination thereof. The one or more catheters may be configured to house, contain and/or protect any size or gauge needle with sheath. For example, the one or more catheters may house, contain, and/or protect about a 22 gauge needle or less, about a 21 gauge needle, about a 19 gauge needle or greater, etc. An outer surface of the one or more catheters may include one or more echogenic features or scribes. The one or more catheters may include one or more echogenic features so that the position and orientation of the catheter, the device, the needle, the needle tip, or a combination thereof can be viewed. The one or more catheters may include or define a hole or opening at a distal end, a proximal end, at a region in between, or a combination thereof so that one or more devices or instruments can pass therethrough. The one or more catheters may include or define an inner surface, an inner diameter, an inner portion, or a combination thereof that is dimensioned to generally conform to the outer diameter of the one or more needles or needle sheaths.

The one or more sheaths may function to be advanced into the anatomy for safe delivery of the one or more needles. The one or more sheaths may also function to provide medicine, therapy, or both to the anatomy. The one or more sheaths may also function to provide, develop, or have a local vacuum to a distal end or at a distal tip thereof. The one or more sheaths may be advanced towards and retracted from the region of interest via one or more catheters, devices, bronchoscopes, a handle, or a combination thereof. The one or more sheaths may be at least partially contained within the catheter. The one or more sheaths may be moved, advanced, retracted, or a combination thereof in the catheter. The one or more sheaths may have a length that extends along a longitudinal axis, a sheath axis, or both. The one or more sheaths may have a constant cross section, a varying cross section, a tapered cross section, an irregular cross section, or a combination thereof. The cross section of the one or more sheaths may be generally circular, oval, irregular, or any other suitable shape. The one or more sheaths may be generally hollow. The one or more sheaths may include a generally concentric outer diameter and inner diameter. The one or more sheaths may have an outer diameter and an inner diameter, one or more of which may have a constant size along a length of the sheath. The one or more sheaths may have an outer diameter and an inner diameter, one or more of which may vary, taper, slope, change, or a combination thereof. The one or more sheaths may be formed from a single material, or may be formed from one or more materials. The one or more sheaths may be fabricated from any material suitable for use in medical procedures. The one or more sheaths may be made of a polymer or other similar material. The one or more sheaths may be generally rigid, generally flexible, or both. The one or more sheaths may include one or more portions or sections that are generally rigid, one or more portions or sections that are generally flexible, or both. The one or more sheaths may be at least partially flexible, bendable, articulable, or a combination thereof so that access to regions of interest can be easily obtained. The one or more sheaths may bend or articulate about 15 degrees or more, about 45 degrees or more, about 60 degrees or more, about 0 degrees or more, about 110 degrees or more, or even about 130 degrees or more. The one or more sheaths may include one or more hypotubes. The one or more sheaths may be relatively smooth and able to freely slide, rotate, or otherwise move within a catheter, a bronchoscope, a device, the anatomy, or a combination thereof. The one or more sheaths may include one or more holes, ports, slots, apertures, openings, the like, or a combination thereof at the distal end, a proximal end, or a location therebetween. The one or more sheaths may include one or more holes, ports, slots, the like or a combination thereof for introducing medicine or therapy to the anatomy.

The one or more sheaths may be any size or gauge. That is, the one or more sheaths may be about 22 gauge or less, about 21 gauge, or about 19 gauge or greater, etc. The one or more sheaths may include a combination of two or more gauges. That is, for example, a proximal portion of the sheath may be about 21 gauge and a distal portion of the sheath may be about 19 gauge, or vice versa. The one or more sheaths may include two or more portions that are joined together fixedly, permanently, temporarily, or a combination thereof and those portions may have different memory shapes. The two or more portions may be the same gauge, or may be different gauges. The sheath may include one or more, or even two or more echogenic markings or scribes. The one or more echogenic features may function to enhance visibility. The one or more echogenic features may function to create one or more echogenic reflections during ultrasonic imaging so that a position or location of the sheath within the anatomy can be determined. The one or more echogenic features may be or may include one or more scribes, bands, slots, segments, shapes, surfaces, recesses, roughened surfaces, embedded material(s), coatings, grooves, serrations, notches, or a combination thereof. The one or more echogenic features may be one or more dimples, scallops, spiral scribes, helixes, squiggles, angled squiggles, jig-saws, symmetrical shapes, asymmetrical shapes, patterns, dots, dashes, lines, formations, or a combination thereof.

The one or more needles may function to be advanced into the anatomy to penetrate a site or region of interest. The one or more needles may function to puncture a region of interest so that the tissue sampling may occur. The one or more needles may also function to provide medicine, therapy, or both to the anatomy. The one or more needles may also function to provide, develop, or have a local vacuum to a distal end or at a distal tip thereof. The one or more needles may be advanced towards and retracted from the region of interest via one or more catheters, devices, bronchoscopes, a needle handle, or a combination thereof. The one or more needles within a sheath(s) may be at least partially contained within the catheter. The one or more needles may be moved, advanced, retracted, or a combination thereof in the catheter or in the sheath. The one or more needles may have a length that extends along a longitudinal axis, a needle axis, or both. The one or more needles may have a constant cross section, a varying cross section, a tapered cross section, an irregular cross section, or a combination thereof. The cross section of the one or more needles may be generally circular, oval, irregular, or any other suitable shape. The one or more needles may be generally hollow. The one or more needles may include a generally concentric outer diameter and inner diameter. The one or more needles may have an outer diameter and an inner diameter, one or more of which may have a constant size along a length of the needle or the sheath. The one or more needles may have an outer diameter and an inner diameter, one or more of which may vary, taper, slope, change, or a combination thereof. The one or more needles may be formed from a single material, or may be formed from one or more materials. The one or more needles may be fabricated from any material suitable for use in medical procedures. The one or more needles may be made from a metal or metal alloy, such as stainless steel, nitinol, or the like. The one or more needles may include a polymer or other suitable covering. The one or more needles may be generally rigid, generally flexible, or both. The one or more needles may include one or more portions or sections that are generally rigid, one or more portions or sections that are generally flexible, or both. The one or more needles may be at least partially flexible, bendable, articulable, or a combination thereof so that access to regions of interest can be easily obtained. The one or more needles may bend or articulate about 15 degrees or more, about 45 degrees or more, about 60 degrees or more, about 0 degrees or more, about 110 degrees or more, or even about 130 degrees or more. The one or more needles may be constructed from one or more hypotubes. The one or more needles may be constructed from one or more hypotubes that are relatively smooth and able to freely slide, rotate, or otherwise move within a catheter, a bronchoscope, a device, the anatomy, or a combination thereof. The one or more needles may include one or more holes, ports, slots, apertures, openings, the like, or a combination thereof at the distal end, a proximal end, or a location therebetween. The one or more needles may include one or more holes, ports, slots, the like or a combination thereof for tissue sample collection; for introducing a stylet into the needle; for introducing the stylet into the anatomy; for introducing medicine or therapy to the anatomy; or a combination thereof.

The one or more needles may be any size or gauge. That is, the one or more needles may be about 22 gauge or less, about 21 gauge, or about 19 gauge or greater, etc. The one or more needles may include a combination of two or more gauges. That is, for example, a proximal portion of the needle may be about 21 gauge and a distal portion of the needle may be about 19 gauge, or vice versa. The one or more needles may include two or more portions that are joined together fixedly, permanently, temporarily, or a combination thereof and those portions may have different memory shapes. The two or more portions may be the same gauge, or may be different gauges. One or both of the portions may include an interior size or region that is generally the same size as the one or more stylets. That is, the one or more stylets may substantially occupy some, most, or all of the interior of the one or more needles, needle portions, or both. One or both of the needle portions, the needle, or both may be slightly larger than the one or more stylets, so that the stylets only occupy some of the interior space or region of the one or more needles, needle portions, or both. The one or more needles may include an elongated section, member, or shaft and a distal tip or needle tip. The elongated section, the needle tip, or both may include one or more, or even two or more echogenic markings or scribes. The one or more echogenic features may function to enhance the visibility of the catheter, the needle, the needle tip, or a combination thereof. The one or more echogenic features may function to create one or more echogenic reflections during ultrasonic imaging so that a position or location of the catheter, the needle, and/or the needle tip within the anatomy can be determined. The one or more echogenic features may be or may include one or more scribes, bands, slots, segments, shapes, surfaces, recesses, roughened surfaces, embedded material(s), coatings, grooves, serrations, notches, or a combination thereof. The one or more echogenic features may be one or more dimples, scallops, spiral scribes, helixes, squiggles, angled squiggles, jig-saws, symmetrical shapes, asymmetrical shapes, patterns, dots, dashes, lines, formations, or a combination thereof. The one or more needles may include a distal tip.

The distal end of the needle, the distal tip, the needle tip, or a combination thereof may be configured to function as a piercing tip or feature so that cells, tissue, foreign matter, or a combination thereof can be obtained. The needle tip may be angled, sharply angled, beveled, flat, or a combination thereof so that tissue samples can be cut, cored, scraped from a site or region of interest. The needle tip may include a notched portion, a recessed portion, and/or a lancet tip or feature. A local vacuum may be created or formed at a distal end of the needle, a distal portion, or a needle tip so that tissue samples, foreign matter, or both can be aspirated or moved into the needle, the sample storage area, or both. The one or more needle tips and corresponding sheath may be contained within the one or more catheters as the catheter is advanced through the anatomy towards the site or region of interest. The one or more sheaths and the needle tips may be advanced or extended past a distal end of the one or more catheters when the catheter is near the region of interest. The one or more needle tips may be generally rigid, flexible, or both. The distal end, the needle tip, or both may include one or more echogenic features. The one or more needles may include one or more sample storage areas. An example needle is shown in PCT Application Ser. No. PCT/US16/20011 filed Feb. 29, 2016, which is hereby incorporated by reference.

The one or more stylets may function to steer or guide the one or more needles, catheters, devices, or a combination thereof around the anatomy to the region of interest. The one or more stylets may be disposed within the needle such that the distal ends of the stylet and the needle are substantially aligned. The one or more stylets may function to block or prevent debris (i.e., tissue, blood, and the like) from entering the needle as the needle is advanced towards a site or region of interest. The one or more stylets may be formed from a single material, or may be formed from one or more materials. The one or more stylets may be fabricated from any suitable material. The one or more stylets may be made from a metal or metal alloy, such as stainless steel, nitinol, or the like. The one or more stylets may be formed from a shape memory material (i.e., metal or polymer). The one or more stylets may comprise a polymer or other suitable covering over at least a portion of the length of the stylets. The one or more stylets may be at least partially rigid, at least partially flexible, or both. The one or more stylets may include one or more portions (i.e., a distal portion, a proximal portion, or a portion in between) that are at least partially rigid, at least partially flexible, or both. The one or more stylets may be at least partially flexible, bendable, articulable, or a combination thereof so that the stylet can be positioned along a central lumen, opening, and/or interior portion of the needles. The one or more stylets may bend or articulate about 15 degrees or more, about 45 degrees or more, about 60 degrees or more, about 90 degrees or more, about 110 degrees or more, or even about 130 degrees or more. The one or more stylets may have a generally uniform cross section, or the cross section may be variable. At least a portion of the outer surface of the one or more stylets may be substantially the same size as the interior of one or more needle portions of the one or more needles so that the stylet substantially occupies some, most, or all of the interior of the needle. The one or more stylets may be advanced, actuated, or moved from a retracted position to an advanced position. In the retracted position, the distal end of the one or more stylets may be offset or retracted from the distal end of the one or more needles. The one or more stylets may include one or more notched portions, recesses, cut-outs, or grooves. The one or more notched portions, recesses, cut-outs, or grooves may be located at a distal end, or at a location between the distal and proximal ends of the stylet.

The handle includes various operational components. The first one of the operational components may control motion of the needle sheath and the needle relative to the catheter. A second one of the operational components may control motion of the needle relative to the sheath and the catheter. A third one of the operational components may control motion of the stylet relative to the needle, the sheath and/or the catheter. A fourth one of the operational components to keep the stylet from moving in a proximal direction until the needle is positioned as desired.

FIG. 1-1 illustrates an example needle aspiration device 20 (e.g., transbronchial needle aspiration (TBNA) device) in a deactivated position and FIG. 1-2 illustrates the device 20 in an activated position. The device 20 includes a handle body 26, a needle actuator 28, a stylet knob 30 and a Luer component 32. The handle body 26 is attached to a proximal end of a sheath 34. The needle actuator 28 includes a shaft portion 36 coupled to a handle portion 38. The shaft portion 36 is slidably received within a cavity (i.e., lumen) of the handle body 26. The needle actuator 28 receives and is attached to a proximal end of a needle 40. The stylet knob 30 is attached to a proximal end of a stylet (not shown) that is received within the needle 40, the handle body 26 and the needle actuator 28. The stylet knob 30 is received at a proximal end of the Luer component 32. A distal end of the Luer component 32 is attached to a cavity of the handle portion 38 of the needle actuator 28.

In the deactivated position, the distal end of the needle 40 is retracted within the sheath 34 (FIG. 1-1). In the activated position, the distal end of the needle 40 is exposed beyond the distal end of the sheath 34 (FIG. 1-2).

The device 20 may be used for sampling of tissue, for example pulmonary tissue. In some embodiments, the device 20 is configured to be used in thoracoscopic, laparoscopic, transcutaneous, and/or percutaneous procedures. In some such embodiments, the device 20 can be navigated to the nodule or other site of interest within the body via fluoroscopy, tomography or other external visualization techniques. In some configurations, the needle sheath 34 with the needle 40 and stylet can be inserted into a bronchoscope. Various types of bronchoscopes may be used, including but not limited to the BF-P180 bronchoscope manufactured by Olympus®. Bronchoscopes using ultrasound probes or other visualization devices also can be used, including the EBUS® scope manufactured by Olympus®. The sheath 34 is received within the bronchoscope (and its working channel).

In some configurations, the sheath 34 can be inserted into an airway so that the distal end reaches or is placed proximate a region of tissue to be treated and/or sampled. Other configurations also are possible. For example, when used relative to other body tissues and/or in other body lumens (e.g., during intestinal or colonoscopy treatments), the device 20 can be loaded into other types of endoscopes. As will be described in greater detail below, the needle 40 is able to pierce through an airway wall or lumen after the sheath 34 is placed proximate a region of targeted tissue, such as a lung nodule, for example but without limitation. In other words, after the sheath 34 passes along one or more airway of the lung, the needle 32 can be used to pierce an airway wall or lumen to gain access to tissue, nodules or the like outside of the airway. In some configurations, the sheath 34 can be passed through an airway and then extend into tissue outside of the airway while remaining within the pleurae.

As shown in FIG. 2, a sheath insert 50 is received within a distal end of the sheath 34. When in a deactivated state, the needle 40 is sized to be housed within the sheath insert 50. The sheath 34 may be formed of extruded Polytetrafluoroethylene (PTFE) or comparable polymer tubing. The sheath insert 50 may be formed of stainless steel or comparable material including non-metals exhibiting similar physical characteristics and/or performance.

The sheath insert 50 is inserted (with force and/or heat) into an extruded (raw) PTFE tube (i.e., the sheath 34). This causes the sheath 34 to expand, thus making room for the sheath insert 50. The sheath 34 applies a radial force to the sheath insert 50, thus creating a "joint" between the sheath 34 and the sheath insert 50. The outer diameter of the sheath 34 increases beyond an original dimension where the sheath insert 50 is located. See FIGS. 2-4.

Alternatively, the sheath 34 may be formed around the sheath insert 50 by layering sheath material to contain the positioned sheath insert 50 component. This can be accomplished using various techniques such as thermal forming or polymer film casting. The outer diameter of the sheath 34 can be maintained to a consistent desired dimension if needed.

In one embodiment, the distal end of the PTFE tubing is heated in a thermal forming process to reduce any sharp edges. This improves travel of the sheath 34 through/around tissue and may help to keep the sheath insert 50 in its initial position.

The sheath insert 50 minimizes the risk of snagging of the needle tip when advancing through the sheath 34, puncturing a scope working channel with the needle tip and kinking of the sheath 34 when it is over-extended out of the scope.

Figure 3:
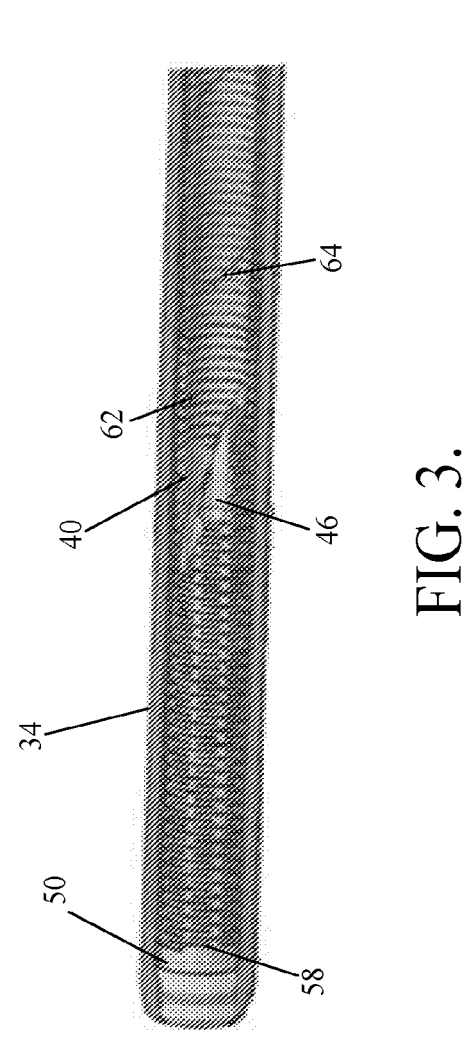
FIG. 3 is a partial see-through view of the distal end of the sheath and needle of the device shown in FIGS. 1-1 and 1-2 when in the deactivated state.
Figure 4:
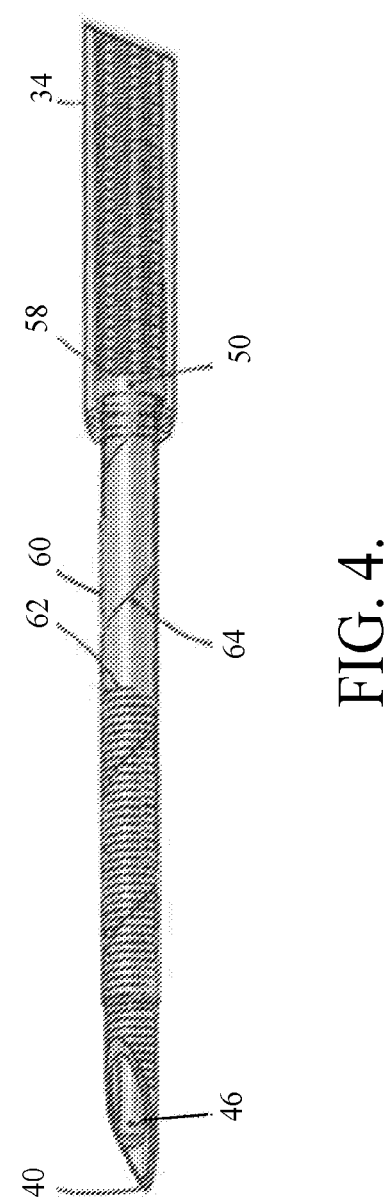
FIG. 4 is a partial see-through view of the distal end of the sheath and needle of the device shown in FIGS. 1-1 and 1-2 when in the activated state.

In one embodiment, cuts are applied to the sheath insert 50. The cuts may pass from an exterior surface to an interior surface of the sheath insert 50. Various cuts patterns may be applied to the sheath insert 50. In one example, as shown in FIGS. 2-4, cuts 58 through the sheath insert 50 are interrupted cuts formed either circularly or spirally. The cuts 58 improve the flexibility of the sheath insert 50 without causing significant exposure of the needle 40 received within a lumen of the sheath insert 50 during operation. The cuts 58 may be made using various methods, such as laser cutting, electrostatic discharge machining, chemical or water etching, or traditional machining.

In one embodiment, the kerf width of the cuts 58 may be between 0.005 inches (0.127 mm) and 0.0005 inches (0.0127 mm) or an appropriate value that would keep the tip of the needle 40 from snagging.

As shown in FIG. 4, the needle 40 includes a heat shrink layer 60 that has a distal end located near the distal end of the needle 40 and a proximal end that may extend all the way the needle actuator 28. The heat shrink layer 60 maintains a vacuum within the lumen of the needle 40. This makes it possible to draw material into the needle 40 with suction. The needle 40 also include a spiral scribe 62 for improving visibility under ultrasound (echogenicity feature) and a spiral cut 64 for improving flexibility. Other scribe and cut patterns may be used.

EMBODIMENTS

A. A needle apparatus comprising: a handle; a needle having a proximal end connected to the handle; and a sheath having a lumen configured to receive of the needle, the sheath comprising: a proximal end connected to the handle; a distal end; a lumen passing from the proximal end to the distal end of the sheath; and a tube received within the lumen at the distal end of the sheath.

B. The needle apparatus of A, wherein an outside diameter of the tube is greater than a diameter of the lumen of the sheath.

C. The needle apparatus of A or B, wherein an inside diameter of the tube is greater than or equal to a diameter of the lumen of the sheath.

D. The needle apparatus of any of A-C, wherein the tube comprises stainless steel.

E. The needle apparatus of D, wherein the tube comprises a plurality of cuts.

F. The needle apparatus of E, wherein the plurality of cuts are radial cuts.

G. The needle apparatus of any of E or F, wherein the plurality of cuts are spiral cuts.

H. The needle apparatus of any of E-G, wherein the plurality of cuts are overlapping cuts.

I. The needle apparatus of any of A-H, wherein the sheath comprises polytetrafluoroethylene.

J. A method comprising: applying heat to a polymer sheath for a needle, the sheath comprising a lumen extending from a proximal end to a distal end, wherein the proximal end of the sheath is configured to be attached to a handle; and applying a force to at least one of the sheath or a metal tube until the tube is fully received with in the sheath, wherein the sheath expands radially at a region occupied by the metal tube.

K. The method of J, wherein an outside diameter of the tube is greater than a diameter of the lumen of the sheath before tube insertion.

L. The method of any of J or K, wherein an inside diameter of the tube is greater than or equal to a diameter of the lumen of the sheath before tube insertion.

M. The method of any of J-L, further comprising making a plurality of interrupted cuts into the tube.

N. The method of M, wherein the plurality of interrupted cuts are radial cuts.

O. The method of any of M or N, wherein the plurality of interrupted cuts are spiral cuts.

P. The method of any of M-O, wherein the plurality of interrupted cuts are overlapping cuts.

Q. The method of any of J-P, wherein the tube is stainless steel.

R. The method of any of J-Q, wherein the polymer is polytetrafluoroethylene.

S. The method of any of J-R, further comprising thermal forming the sheath distal from a distal end of the tube.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

The invention claimed is:

1. A method comprising:
providing a tube including a plurality of interrupted cuts through a sidewall of the tube to increase flexibility of the tube;
applying heat to a distal end portion of a polymer sheath for a needle, the sheath comprising a lumen extending from a proximal end to a distal end of the sheath, wherein the proximal end of the sheath is configured to be attached to a handle; and
subsequent to applying the heat to the distal end portion of the sheath, inserting the tube into a distal end of the lumen of the sheath, by applying a force to at least one of the sheath or the tube until a distal end of the tube is within the distal end of the sheath and the tube is fully received within the sheath, wherein the inserting results in the distal end of the sheath expanding radially at a region occupied by the tube resulting in the region of the sheath including a first outer diameter and the sheath proximal from the region having a second outer diameter, the first outer diameter is greater than the second outer diameter.

2. The method of claim 1, wherein the providing the tube includes obtaining the tube having an outside diameter greater than a diameter of the lumen of the sheath before inserting the tube into the polymer sheath.

3. The method of claim 2, wherein the obtaining the tube includes an inside diameter of the tube that is greater than or equal to the diameter of the lumen of the sheath before applying the force to the at least one of the sheath or the tube.

4. The method of claim 1, further comprising making the plurality of interrupted cuts through the sidewall of the tube.

5. The method of claim 4, wherein making the plurality of interrupted cuts includes making radial cuts.

6. The method of claim 4, wherein making the plurality of interrupted cuts includes making spiral cuts.

7. The method of claim 4, wherein making the plurality of interrupted cuts includes making overlapping cuts.

8. The method of claim 1, wherein the tube is stainless steel.

9. The method of claim 1, wherein the polymer sheath is made from polytetrafluoroethylene.

10. A sheath device comprising:
a handle;
a sheath including:
a distal end portion extending proximally from a distal end of the sheath for a first length and having a first outer diameter;
a proximal end connected to the handle, the proximal end having a second outer diameter; and
a lumen passing from the proximal end to the distal end of the sheath, the lumen including a first inner diameter proximal of the distal end portion; and
a tube including a longitudinal length equal to the first length, the tube received within the lumen at the distal end of the sheath, wherein the tube expands a distal portion of the lumen to generate the first outer diameter of the distal end portion,
wherein the first outer diameter is collocated longitudinally with the tube and extends the length of the tube,
wherein the first outer diameter is greater than the second outer diameter and the tube includes an inner diameter greater than or equal to the first inner diameter of the lumen, and
wherein a proximal end of the tube is collocated with a proximal end of the distal end portion of the sheath and a distal end of the tube is collocated with a distal end of the distal end portion.

11. The sheath device of claim 10, wherein an outer diameter of the tube is greater than the first inner diameter of the lumen at the proximal end of the sheath.

12. The sheath device of claim 10, wherein the inner diameter of the tube is greater than or equal to the first inner diameter of the lumen at the proximal end of the sheath.

13. The sheath device of claim 10, wherein the tube is stainless steel.

14. The sheath device of claim 13, wherein the tube comprises a plurality of cuts.

15. The sheath device of claim 14, wherein the plurality of cuts are radial cuts.

16. The sheath device of claim 14, wherein the plurality of cuts are spiral cuts.

17. The sheath device of claim 14, wherein the plurality of cuts are overlapping cuts.

* * * * *